United States Patent [19]

Buckler et al.

[11] Patent Number: 4,495,281

[45] Date of Patent: Jan. 22, 1985

[54] TRICYCLIC ANTIDEPRESSANT DRUG IMMUNOGENS, ANTIBODIES, LABELED CONJUGATES, AND RELATED DERIVATIVES

[75] Inventors: Robert T. Buckler, Edwardsburg, Mich.; Frederick E. Ward, Elkhart, Ind.

[73] Assignee: Miles Laboratories, Inc., Elkhart, Ind.

[21] Appl. No.: 435,633

[22] Filed: Oct. 21, 1982

[51] Int. Cl.$^3$ .................... A61K 39/385; C07G 7/00; C12N 9/96; G01N 33/54

[52] U.S. Cl. .................... 435/7; 260/112 R; 260/112 B; 260/112.5 R; 260/121; 424/85; 424/88; 435/188; 436/528; 436/536; 544/47

[58] Field of Search .............. 260/112 R, 112 B, 121; 424/85, 88; 435/7, 188; 436/528, 536

[56] References Cited

U.S. PATENT DOCUMENTS

| | | | |
|---|---|---|---|
| 3,817,837 | 6/1974 | Rubenstein et al. | 435/7 |
| 4,043,989 | 8/1977 | Schneider et al. | 424/85 X |
| 4,058,511 | 11/1977 | Singh | 260/112 B |
| 4,213,893 | 7/1980 | Carrico et al. | 424/177 X |
| 4,223,013 | 9/1980 | Hu et al. | 424/85 |
| 4,238,565 | 9/1980 | Hornby et al. | 435/7 |
| 4,275,160 | 6/1981 | Singh et al. | 435/188 |
| 4,279,992 | 7/1981 | Boguslaski et al. | 435/188 X |
| 4,288,553 | 9/1981 | Singh et al. | 260/121 X |
| 4,446,065 | 5/1984 | Lin et al. | 260/112 R |

FOREIGN PATENT DOCUMENTS 1552607  9/1979  United Kingdom.

OTHER PUBLICATIONS

Psychopharm. Comm., 1(4), 421–429, (1975), Spector et al.
J. Anal. Tox 1, 236–243, (1977), Kaul et al.
Lancet, 1214(977), Aherne et al.
Br. J. Clin. Pharm., 3:561–565, (1976), Aherne et al.
Clin. Chem., 24(1), 36–40, (1978), Read et al.
Br. J. Clin. Lab. Invest., 40:191–197, (1980), Brunswick et al.

Primary Examiner—Howard E. Schain
Attorney, Agent, or Firm—Andrew L. Klawitter

[57] ABSTRACT

Tricyclic antidepressant drug (e.g., imipramine, desipramine, amitriptyline, or nortriptyline) immunogens, antibodies prepared therefrom, labeled conjugates, synthetic intermediates, and the use of such antibodies and labeled conjugates in immunoassays for determining such drug. The immunogens comprise the drug coupled at its 2'-position to an immunogenic carrier material. Similarly, the labeled conjugates and synthetic intermediates are 2'-derivatives of the drug or a precursor thereof. The antibodies and labeled reagents are particularly useful in certain homogeneous nonradioisotopic immunoassays for measuring tricyclic antidepressant drugs in biological fluids such as serum.

21 Claims, 4 Drawing Figures

TRICYCLIC ANTIDEPRESSANT DRUG IMMUNOGENS, ANTIBODIES, LABELED CONJUGATES, AND RELATED DERIVATIVES

BACKGROUND OF THE INVENTION

1. Field of the Invention

This invention relates to novel derivatives of tricyclic antidepressant drugs. The derivatives pertain to immunoassays for determining tricyclic antidepressant drugs in liquid media such as biological fluids and include immunogens used to stimulate production of antibodies to the drugs in host animals by conventional techniques. Also provided are labeled conjugates used as reagents, along with the antibodies, in particularly preferred immunoassays. Intermediates in the synthesis of the aforementioned immunogens and labeled conjugates are also provided.

The tricyclic antidepressants are a recognized class of structurally related drugs used for the treatment of depression [*The Pharmacological Basis of Therapeutics*, 5th ed., ed. Goodman and Gilman, MacMillan Publ. Co. (New York 1975) pp. 174 et seq]. All of the drugs have an annealated three ring nucleus, a "tricyclic" nucleus, which is often, but by no means exclusively, dibenzazepinyl, dibenzocycloheptadienyl, dibenzoxepinyl, or phenothiazinyl in nature. A further common feature found in this class of compounds is the presence of a side chain of substantial length off one of the atoms, usually carbon or nitrogen, in the central ring of the tricylic nucleus. The most commonly administered drugs of this class are imipramine, desipramine, amitriptyline, nortriptyline, protriptyline, doxepin, and desmethyldoxepin.

Because of large individual variation in steady state concentrations of tricyclic antidepressants in patients receiving the same therapeutic dose and a correlation between blood levels and clinical response, it is desirable to monitor the concentration of the drugs in the blood of patients under treatment for depression [Kaul et al, *J. Anal. Toxicol.* 1: 236–243 (1977)]. Immunoassay is a useful analytical technique for measuring the concentrations of substances (analytes) appearing in biological fluids in the range in which the tricyclic antidepressants appear in blood. In order to establish an immunoassay for a particular analyte it is necessary to synthesize appropriate derivatives of the drug in order to obtain immunogens by which to stimulate specific antibody production and labeled conjugates by which to monitor the immunoassay reaction.

2. Description of the Prior Art

The determination of tricyclic antidepressants by immunoassay is known [Kaul et al, supra]. Homogeneous immunoassays for determining various analytes including drugs are described in U.S. Pat. Nos. 4,279,992; 4,238,565; and 3,817,837 and in British Pat. No. 1,552,607.

Immunogen conjugates, comprising tricyclic antidepressants coupled to conventional immunogenic carrier materials, useful in stimulating the production of antibodies to the drug in animals are described in the literature. Conjugation of side arm derivatives are described in Brunswick et al, *Br. J. Clin. Lab. Invest.* 40: 191–197 (1980), Aherne et al, *Br. J. Clin. Pharm.* 3: 561–565 (1976), and U.S. Pat. No. 4,207,307. All of these side arm derivatives involve modification of the drug at the terminal amine group on the side arm. Derivatization off one of the rings is described in Read et al, *Postgrad. Med. J.* 53(Suppl 4): 110–116(1977), Read et al, *Clin. Chem.* 24(1): 36–40(1978), and U.S. Pat. Nos. 4,223,013 and 4,275,160. Spector et al, *Psychopharm. Commun.* 1 (4): 421–429 (1975) describe a desipramine immunogen of undefined structure, although the authors believe that conjugation is off the benzyl ring. Immunogens of the related drug carbamazepine with conjugation off its somewhat shortened side arm are described in U.S. Pat. No. 4,058,511.

The state-of-the-art of preparing antibodies to haptens such as drugs is represented by Weinryb et al, *Drug Metabolism Reviews* 10: 271(1979); Playfair et al, *Br. Med. Bull.* 30: 24(1974); Broughton et al, *Clin. Chem.* 22: 726(1976); and Butler, *J. Immunol. Meth.* 7: 1(1975) and *Pharmacol. Rev.* 29(2): 103–163(1978).

Labeled conjugates, comprising the analyte or a derivative or other analog thereof, coupled to a labeling substance are variously described in the literature, e.g., the aforementioned U.S. Pat. No. 4,279,992, wherein the label is the fluorogenic enzyme substrate β-galactosyl-umbelliferone (βGU), and U.S. Pat. No. 4,213,893, wherein the label is flavin adenine dinucleotide (FAD).

Literature pertaining to the derivatization of tricyclic antidepressants and related compounds is referred to in the ensuing text.

SUMMARY OF THE INVENTION

The present invention uniquely provides reagents for use in tricyclic antidepressant drug immunoassays involving the coupling to, or derivatization of, the drug at the 2'-position, herein defined to be the second carbon atom of the side arm off the central ring of the tricyclic nucleus. Using a three circle symbol to represent the tricyclic nucleus, such derivatives have the general formula:

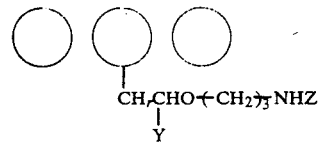

wherein r is 1 or 2 depending on whether the associated carbon atom is bonded to the tricyclic nucleus by a double or single bond, Y is any appropriate group, usually the residual portion of the side arm in the involved drug, and Z is hydrogen, an extension or bridge group terminating in a group reactable or able to be activated to react with available groups in an immunogenic carrier or a labeling molecule, an immunogenic carrier coupled directly through carboxyl groups or through appropriate connecting links, or a labeling molecule, e.g., βGU or FAD, or derivative thereof, coupled directly or through appropriate connecting links.

A central feature of the present invention is the ability to synthesize tricyclic antidepressant derivatives substituted at the 2 -carbon position on the side chain (the 2'-position) with an omega-aminoalkyl group of the formula $-O-(CH_2)_3NH_2$. This is principally accomplished by forming the 2'-hydroxy derivative which upon reaction with acrylonitrile yields a cyanoethyl ether derivative which can be reduced to the aminopropyl ether. The amino function then permits a wide variety of well known synthetic routes to be taken to couple the uniquely derivatized drug to immunogenic carriers, yielding immunogens for stimulating antibody production, and to labeling molecules, yielding labeled conjugates used as reagents in immunoassays.

In a preferred embodiment, the present invention provides novel intermediates in the preparation of the 2'-substituted tricyclic antidepressant reagents. Also provided are an improved immunoassay method and reagent means for the determination of the drugs with the use of the novel antibodies of the present invention. The present invention also provides labeled drug conjugates for particularly preferred embodiments of such immunoassay.

DESCRIPTION OF THE PREFERRED EMBODIMENTS

Figure 1:
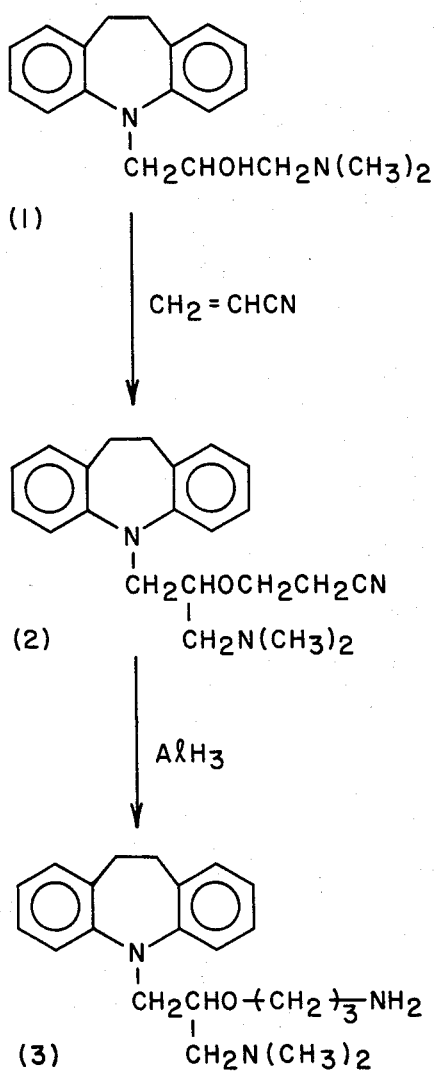
FIGS. 1-4 depict particular synthetic schemes for the preparation of 2'-amino derivatives of each of the four principal tricyclic antidepressants, imipramine, desipramine, amitriptyline, and nortriptyline.
Figure 2:
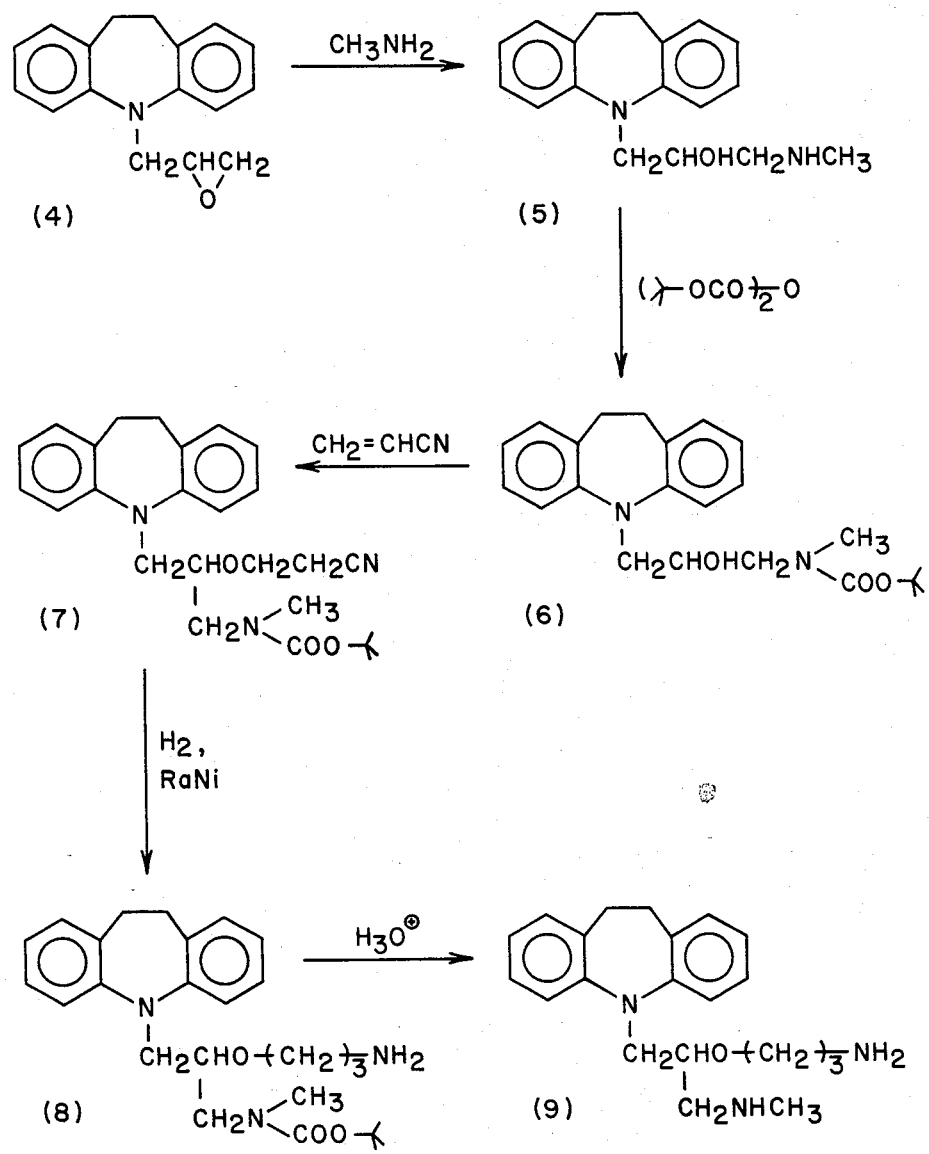
Figure 3:
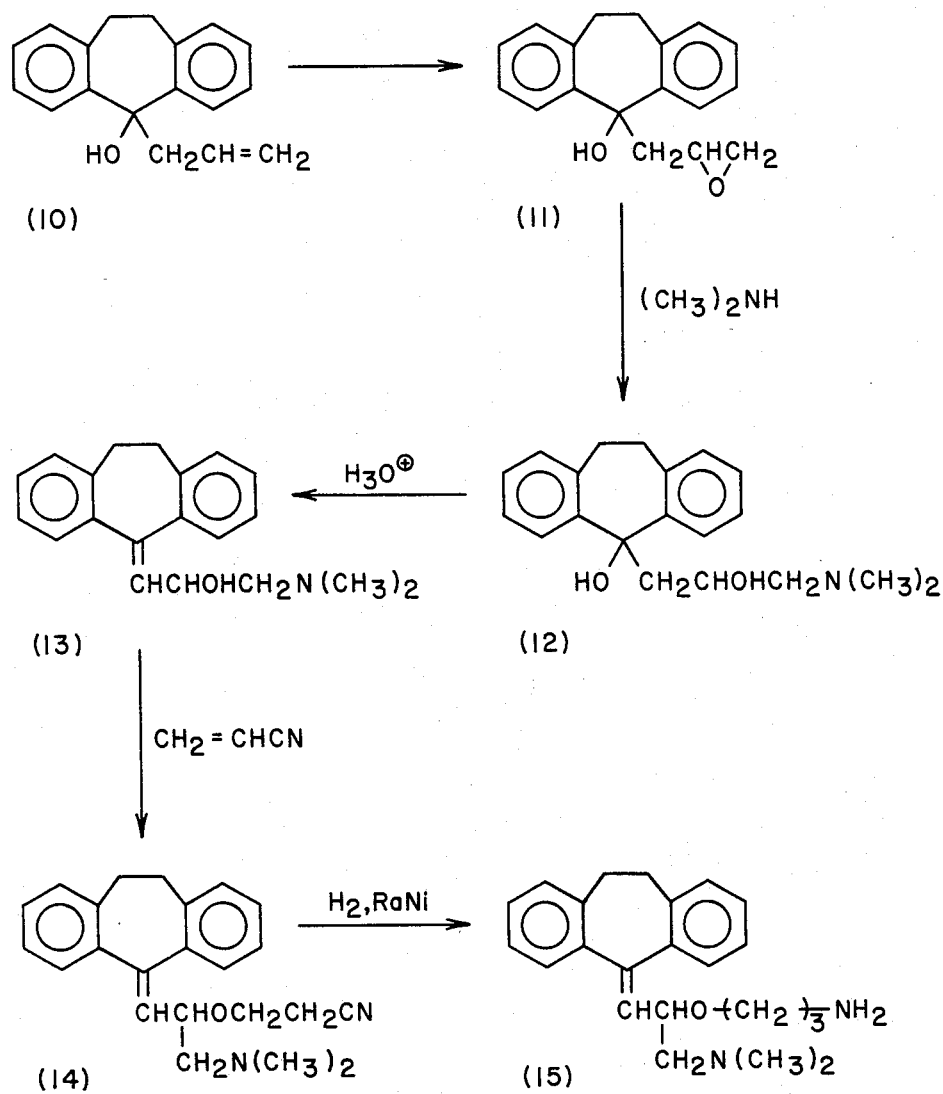
Figure 4:
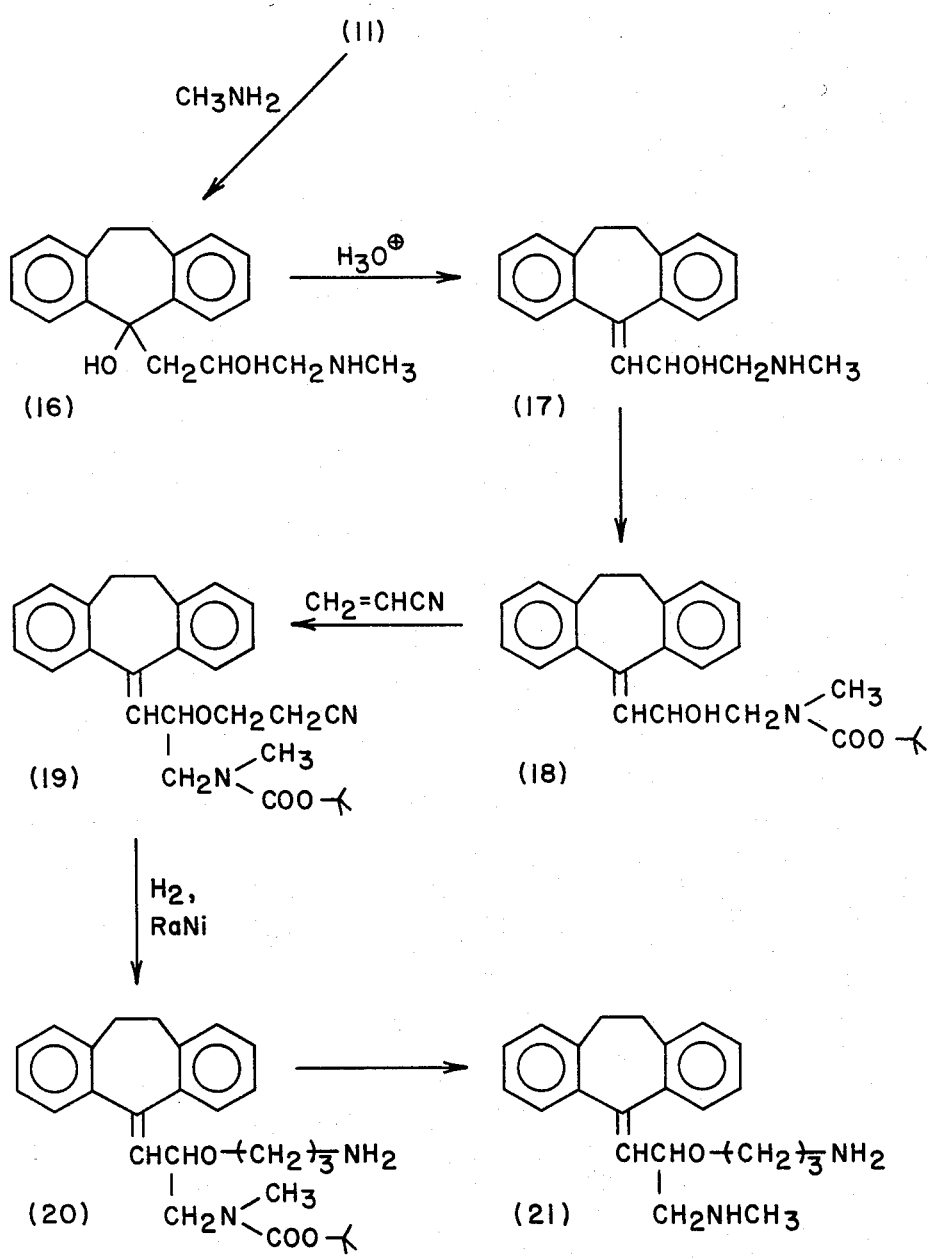

The present invention is applicable to the derivatization of tricyclic antidepressant drugs and related other drugs and compounds, which have the common structural features of an aromatic ring nucleus comprising multiple annealated rings, usually three or four rings, each comprising between 5 and 8 ring atoms selected from carbon, nitrogen, oxygen, and sulfur, with a side chain extending from one of the annealated rings (e.g., the central ring in a three ring nucleus or one of the two central rings in a four ring nucleus). The side chain will comprise from about 4 to about 12 atoms, excluding hydrogen, and will generally be linear alkylamine or alkenylamine. Usually the side chain will be of the formula $=CHCH_2CH_2NR^1R^2$ with the side chain being bonded to a carbon atom in the ring nucleus, or of the formula $-CH_2CH_2CH_2NR^1R^2$ with the side chain being bonded to an appropriate atom, usually carbon or nitrogen, in the ring nucleus. $R^1$ and $R^2$ may be the same or different and are selected from a wide variety of groups, usually hydrogen or carbon-linked substituents, i.e., substituents which end in a carbon atom bonded to the amine nitrogen. Examples of such substituents are linear and branch, substituted and unsubstituted, alkyl, usually lower ($C_{1-6}$) alkyl, and substituted and unsubstituted cycloalkyl when $R^1$ and $R^2$ are taken together. [See "Burger's Medicinal Chemistry", 4th ed., part III, ed. Wolff, John Wiley & Sons (New York 1981), pp. 1018 et seq.]. The invention will now be illustrated with respect to the four principal tricyclic antidepressants (imipramine, desipramine, amitryptyline, and nortriptyline) and the very closely related drugs protriptyline, doxepin, and desmethyldoxepin.

2'-Substituted Derivatives

A. Imipramine-Reaction of 5-(3-dimethylamino-2-hydroxypropyl)-10,11-dihydro-5H-dibenz[b,f]azepine 1 [W. Shindler and F. Haflinger, *Helv. Chim. Acta* 37: 472 (1954)] with acrylonitrile gives the cyanoethyl ether 2 which is reduced with aluminum hydride ($AlH_3$) to the aminopropyl ether 3.

B. Desipramine-5-(2,3-Epoxypropyl)-10,11-dihydro-5H-dibenz[b,f]azepine 4 (Shindler and Haflinger, supra) is condensed with methylamine to give the amino alcohol 5. The secondary amine function of this substance is protected by reaction with di-tert-butyl di-carbonate yielding the amide 6. This is converted to the cyanoethyl ether 7 by treatment with acrylonitrile. Catalytic reduction of 7 by Raney nickel (RaNi) in the presence of hydrogen gas produces the primary amino derivative 8, which, upon treatment with acid, yields the aminopropyl ether derivative 9.

C. Amitriptyline-5-Allyl-5-hydroxy-10,11-dihydro-5H-dibenzo[a,d]cycloheptene 10 [R. D. Hoffsommer et al, *J. Org. Chem.* 28: 1751(1963)] is epoxidized with tert-butylhydroperoxide to produce the epoxy alcohol 11. Reaction with dimethylamine gives the amino-diol 12. Selective dehydration of the tertiary alcohol function in 12 is accomplished by treatment with 3N hydrochloric acid to give the unsaturated amino alcohol 13. The hydroxyl function is alkylated with acrylonitrile to give 14 which, in turn, is hydrogenated to the primary amino compound 15.

D. Nortriptyline-Intermediate 11, supra, is condensed with methylamine to give the secondary amino-diol 16, which is selectively dehydrated, supra, to the unsaturated species 17. The amino group of 17 is protected as the tert-butyloxycarbonyl derivative 18 and treated with acrylonitrile. The product 19 is reduced to the amine 20, which is then de-protected to yield the primary amino derivative 21.

E. Protriptyline-Intermediate 5H-dibenzo[a,d]cycloheptene [Aldrich Chemical Co., Milwaukee, WI] can be alkylated with allyl bromide by the method disclosed in Belgian Pat. No. 634,448; Jan. 3, 1964 [*Chem. Abst.* 61: 4295(1964)]. The terminal double bond can be selectively epoxidized and further transformed into the appropriate amino derivative by the reactions disclosed here for imipramine.

F. Doxepin-Dibenz[b,e]oxepine-11-one [K. Stach and H. Springler, *Angew. Chem.* 74: 31(1972)] can be reacted with allyl magnesium chloride to give 11-allyl-11-hydroxydibenz[b,e]oxepine. Epoxidation of the terminal double bond and reaction with dimethylamine will give 11-(3-dimethylamino-2-hydroxypropyl)-11-hydroxydibenz[b,e]oxepine. Selective dehydration of the tertiary alcohol, by methods similar to that used to prepare the amitriptyline derivative, will produce the doxepin analog of the nortriptyline derivative 17 [c.f., Belgian Pat. No. 623,259; Apr. 5, 1963; *Chem. Abst.* 60: 10659g (1964)]. It can be further transformed to the doxepin amino derivative by the sequence of reactions used for nortriptyline.

G. Desmethyldoxepin-The method described above for doxepin is followed except that methylamine rather than dimethylamine is used in the reaction following epoxidation.

The resulting 2'amino derivatives have the formula:

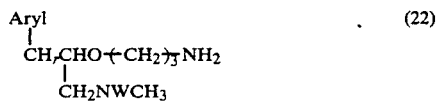

(22)

wherein Aryl represents a tricyclic antidepressant drug nucleus selected from:

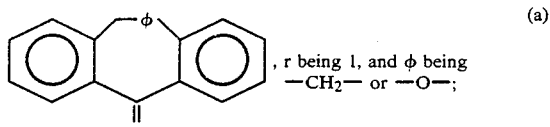

, r being 1, and φ being —$CH_2$— or —O—;

(a)

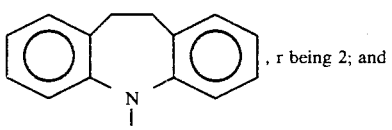, r being 2; and

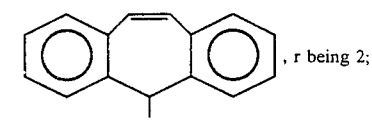, r being 2;

and wherein W is hydrogen or methyl. Such aminoderivatives can be used directly to couple to immunogenic carrier materials or labeling substances, or can be further functionalized to give derivatives of the formula:

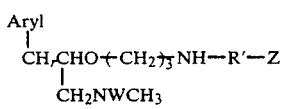 (23)

wherein R' is any appropriate linking group and Z is an appropriate reactive group for coupling to carrier materials or labeling substances (Z commonly being amino, carboxyl, hydroxyl, thiol, or maleimido).

One skilled in the art has a wide variety of linking groups R' that can be introduced to derivatives 23 of the present invention. Exemplary of such choices are linear and branched alkylenes comprising from 1 to as many as 15, more usually 10 or less, and normally less than 6, carbon atoms (e.g., methylene, ethylene, n-propylene, iso-propylene, n-butylene, and so forth). In addition, such alkylenes can contain other substituent groups such as cyano, amino (including substituted amino), acylamino, halogen, thiol, hydroxyl, carbonyl groups, carboxyl (including substituted carboxyls such as esters, amides, and substituted amides). The linking group R' can also contain or consist of substituted or unsubstituted aryl, aralkyl, or heteroaryl groups (e.g., phenylene, phenyethylene, and so forth). Additionally, such linkages can contain one or more heteroatoms selected from nitrogen, sulfur and oxygen in the form of ether, ester, amido, amino, thio ether, amidino, sulfone, or sulfoxide. Also, such linkages can include unsaturated groupings such as olefinic or acetylenic bonds, imino, or oximino groups. Preferably R' will be a chain, usually an aliphatic group, comprising between 1 and 20 atoms, more usually between 1 and 10, excluding hydrogen, of which between 0 and 5 are heteroatoms selected from nitrogen, oxygen, and sulfur. Therefore, the choice of linking group R' is not critical to the present invention and may be selected by one of ordinary skill taking normal precautions to assure that stable compounds are produced.

Similarly, the terminal functional group Z can vary widely, although amino, carboxyl, thiol, hydroxyl, and maleimido are preferred.

When R' is alkylene, a reductive alkylation reaction can be employed. The appropriate 2'-amino derivative 22 can be reacted with an appropriate oxo-alkanoic acid such as 9-oxononanoic acid [W. Rigby, *Nature*, 164, 185 (1949)] in the presence of sodium cyanoborohydride [R. F. Borch, et al, *J. Amer. Chem. Soc.* 93: 2897 (1971)] to give

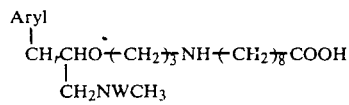

When R' is alkenylene, the preceding synthesis can be modified to yield an alkenylene linking group by substituting a keto-alkenoic acid for the keto-alkanoic acid. For example, the use of 9-oxo-2-decenoic acid [M. Barbier, et al, *Compt. Rendu.* 251: 1135 (1960)] in the above alkylation reaction will yield

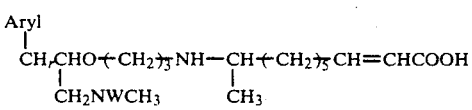

When R' is phenylene, the preceding examples can be modified by replacing the oxo-alkenoic acids with the appropriate aromatic keto acid. Reductive alkylation with 4-[2-(3-carboxypropyl)phenyl]-2-butanone [R. T. Buckler, et al, *European J. Med. Chem.* 12: 465 (1977)] will produce a carboxyl-functionalized tricyclic antidepressant derivative containing a phenylene group in the linking arm and having Z=COOH.

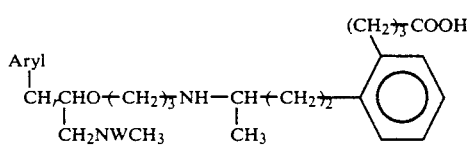

Derivatives 23 having Z=thiol can be prepared by reacting the corresponding primary amino compound 22 with N-succinimidyl-3-(2-pyridyldithio)propionate [J. Charlson, et al, *Biochem. J.* 173: 723 (1978)] or SAMSA reagent [I. M. Klotz and R. E. Heiney, *Arch. Biochem. Biophys.* 95: 605 (1964)] followed by removal of the thiol protecting group.

It will be evident to one of ordinary skill in the art that the above-described synthetic schemes, or simple modifications thereof, can be applied to the derivatization of other tricyclic antidepressant drugs and other structurally related compounds for the purpose of preparing side arm derivatives for coupling to immunogenic carriers or labeling substances without departing from the inventive concept presented here. Examples of such other drugs and compounds to which the present invention may apply equivalently are phenothiazine derivatives such as chloropromazine, prochloroperazine, and trifluoperazine, propazepine, sintamil, iprindole, flupenthixol, α-chlopenthixol, pinoxepin, and maprotiline.

Immunogens

The immunogens of the present invention have the formula:

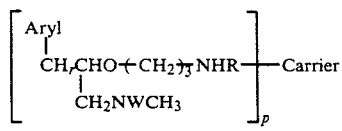

wherein Aryl, r, and W are as defined above, R is a bond (i.e., when coupling amino-derivatives 22 directly to Carrier) or an appropriate linking group (i.e., a residue of —R'—Z remaining from coupling derivatives 23 to Carrier), Carrier is a conventional immunogenic carrier material, and p is the number of tricyclic moieties conjugates to the carrier. The number p is sometimes referred to as the epitopic density of the immunogen and in the usual situation will be on the average from 1 to about 50, more normally from 1 to about 25. Optimal epitopic densities, considering the ease and reproducibility of synthesis of the immunogen and antibody response, fall between about 2 and about 20, more usually between 5 and 15.

The immunogenic carrier material can be selected from any of those conventionally known. In most cases, the carrier will be a protein or polypeptide, although other materials such as carbohydrates, polysaccharides, lipopolysaccharides, nucleic acids and the like of sufficient size and immunogenicity can likewise be used. For the most part, immunogenic proteins and polypeptides will have molecular weights between 5,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins having significant non-proteinaceous constituents, e.g., glycoproteins, and the like. The albumins and globulins of molecular weight between 30,000 and 200,000 are particularly preferred. Further reference for the state-of-the-art concerning conventional immunogenic carrier materials and techniques for coupling haptens thereto may be had to the following: Parker, *Radioimmunoassay of Biologically Active Compounds*, Prentice-Hall (Englewood Cliffs, N.J. USA, 1976); Butler, *J. Immunol. Meth.* 7: 1-24 (1975) and *Pharmacol. Rev.* 29(2): 103-163(1978); Weinryb and Shroff, *Drug Metab. Rev.* 10: 271-283 (1975); Broughton and Strong, *Clin. Chem.* 22: 726-732 (1976); and Playfair et al, *Br. Med. Bull.* 30: 24-31 (1974).

The appropriate 2'-substituted derivatives are couplable to such carrier materials according to well known techniques. For example, the amino derivatives 22 can be attached directly to the carrier by the following means. The amino group of the drug moiety can be attached to amino-containing carriers (e.g., protein or polypeptide carriers) by toluene-2,4-diisocyanate [A. F. Schick and S. J. Singer, *J. Biol. Chem.* 236: 2477 (1961)]; 4,4'-difluoro-3,3'dinitrodiphenyl sulfone [P. S. Cuatrecasas, et al, *J. Biol. Chem.* 244: 406 (1969)]; glutaraldehyde [L. A. Frohman, et al, *Endocrinol.* 87: 1055 (1970)]; bis-imidates [A. Dutton, et al, *Biochem. Biophys. Res. Comm.* 23: 730 (1966)]; and chlorotriazine [T. Lang, et al, *J. C. S. Perkin* 4: 2189 (1977)]. Also, the amino groups of 22 can be coupled to carboxyl-bearing carriers (e.g., again, protein or polypeptide carriers) by common peptide bond-forming reactions by means of mixed anhydrides, activated esters, acyl azide formation, carbodiimides, etc., see *Peptides*, ed. Goodman and Meinhofer, John Wiley & Sons (New York, 1977) p. 6 et seq, and *The Peptides, Analysis, Synthesis, Biology*, Vol. 1, Academic Press (New York, 1979). The same methods apply likewise for attaching carboxylated derivatives 23 (Z=COOH) to amino-bearing carriers.

Thiolated tricyclic derivatives can be prepared from the corresponding amino compounds by the procedure of I. M. Klotz and R. E. Heiney, *Arch. Biochem. Biophys.* 95:605 (1962) and these attached to thiol-containing polymers (IgG or thiolated proteins) by the disulfide exchange procedure [J. Martin, et al, *Biochem.* 20: 4229 (1981)]. Alternately, an amino-containing polymer can be reacted with the reagent MBS and the product coupled to thiol-containing derivatives by the process described by T. Kitagawa and T. Aikawa, *J. Biochem.* 79: 233 (1973).

A multitude of other coupling techniques are available to those of ordinary skill in the art for joining the various 2'-derivatives of the present invention with conventional immunogenic carrier materials.

As applied to the four principal tricyclic antidepressant drugs, the preferred immunogens have the formulae:

(a) for imipramine and desipramine (24)

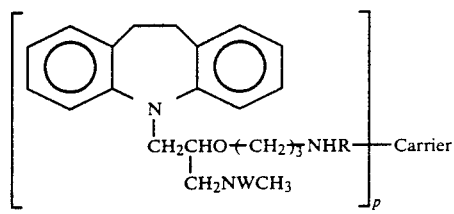

(b) for amitriptyline and nortriptyline (25)

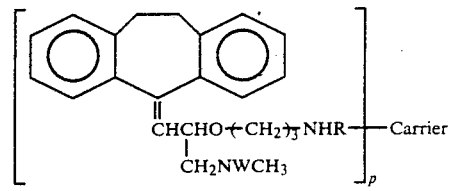

wherein W is hydrogen or methyl, R is a bond or a linking group, Carrier is as defined above, and p is on the average from 1 to about 50.

Antibodies

Preparation of specific antibodies using the present immunogen conjugates may follow any conventional technique. Numerous texts are available describing the fundamental aspects of inducing antibody formation; for example reference may be made to Parker, *Radioimmunoassay of Biologically Active Compounds*, Prentice-Hall (Englewood Cliffs, N.J., USA, 1976). In the usual case, a host animal such as a rabbit, goat, mouse, guinea pig, or horse is injected at one or more of a variety of sites with the immunogen conjugate, normally in mixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. Where desirable, purification steps may be taken to remove undesired material such as nonspecific antibodies before the antiserum is considered suitable for use in performing actual assays.

The antibodies can also be obtained by somatic cell hybridization techniques, such antibodies being commonly referred to as monoclonal antibodies. Reviews of such monoclonal antibody techniques are found in *Lymphocyte Hybridomas*, ed. Melchers et al, Springer-Verlag (New York 1978), *Nature* 266: 495(1977), *Science* 208: 692 (1980), and *Methods in Enzymology* 73 (Part B):3–46(1981).

Immunoassay Techniques

The antibodies prepared from the immunogens of the present invention can be used in any immunoassay method, and the corresponding reagent means, for determining tricyclic compounds, including agglutination techniques, radioimmunoassays, heterogeneous enzyme immunoassays (e.g., U.S. Pat. No. 3,654,090), heterogeneous fluorescent immunoassays (e.g., U.S. Pat. Nos. 4,201,763; 4,171,311; 4,133,639 and 3,992,631), and homogeneous (separation-free) immunoassays. The latter-most are particularly preferred and include such techniques as fluorescence quenching or enhancement (e.g., U.S. Pat. No. 4,160,016), fluorescence polarization (*J. Exp. Med.* 122: 1029(1965), enzyme substrate-labeled immunoassay (U.S. Pat. No. 4,279,992 and U.K. Pat. Spec. No. 1,552,607), prosthetic group-labeled immunoassay (U.S. Pat. No. 4,238,565), enzyme modulator-labeled immunoassay, e.g., using inhibitor labels (U.S. Pat. Nos. 4,134,792 and 4,273,866), enzyme-labeled immunoassay (e.g., U.S. Pat. No. 3,817,837), energy transfer immunoassay (U.S. Pat. No. 3,996,345), chemically-excited fluorescence immunoassay (U.S. Pat. No. 4,238,195) and double antibody steric hindrance immunoassay (U.S. Pat. Nos. 3,935,074 and 3,998,943).

Moreover, the 2'-derivatives of the present invention can be used to prepare the labeled conjugates needed to perform the various immunoassays described above. Appropriate derivatives can be radio-labeled or labeled with fluorescent moieties in accordance with standard methods. Likewise the appropriate labeling moiety for the preferred homogeneous techniques, e.g., an enzyme substrate, a prosthetic group, an enzyme modulator, or an enzyme (which is a protein and can be coupled similarly to the immunogenic carrier as described above) can be coupled to the 2'-derivatives to yield labeled conjugates.

One type of preferred labeled conjugate is that labeled with β-galactosyl-umbelliferone (βGU), having the general formula:

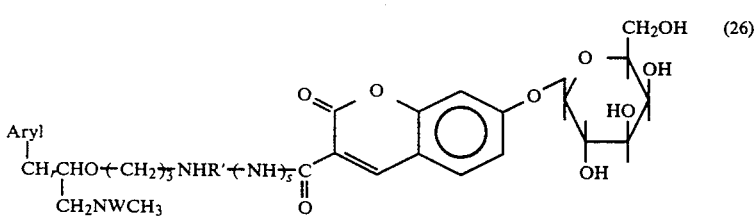

wherein Aryl, r and W are defined above, R' is a bond or an appropriate linking group, and s is 0 or 1. Preferably, such conjugates are prepared by standard peptide condensations of β-galactosyl-umbelliferone carboxylic acid (U.S. Pat. No. 4,226,978) with the appropriate 2'-amino derivative 22, in which case the resulting βGU-drug conjugate 26 will have a bond as R' and s is 0. (26a=βGU-imipramine, 26b=βGU-desipramine, 26c=βGU-amitriptyline, and 26d=γGU-nortriptyline). Alternatively, an appropriate extended arm aminoderivative 23 where Z=NH$_2$ can be coupled by peptide condensation to the βGU-acid. The βGU-conjugates are useful as labeled reagents in substrate-labeled fluorescent immunoassays (SLFIA—see U.S. Pat. No. 4,279,992).

Another preferred type of labeled conjugate is that labeled with flavin adenine dinucleotide (FAD), having the general formula:

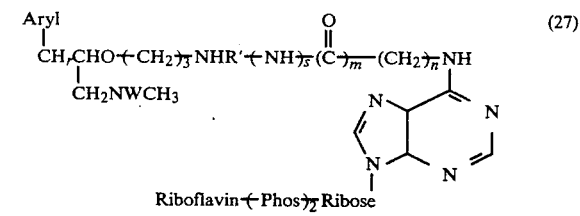

wherein Aryl, r, and W are defined above, R' is a bond or an appropriate linking group, m and s are, independently, 0 or 1 and at least one of m and s is 1; n is an integer from 2 through 10; and Riboflavin-(Phos)$_2$-Ribose represents the riboflavin-pyrophosphate-ribose residue in FAD. In one case, R' is a bond and m=1 and s=0. Such conjugates are formed by peptide condensation of 2'-amino derivatives 22 with carboxylated FAD derivatives (see Examples for preparation of N$^6$—HOOC—(CH$_2$)$_n$—FAD derivatives). In another case, R' is an appropriate linking group and m=s=1. Such conjugates are formed by peptide condensation of an appropriate extended arm 2'-amino derivative 23 with the carboxylated FAD derivatives. The FAD-conjugates are useful as labeled reagents in apoenzyme reactivation immunoassay systems (ARIS—see U.S. Pat. No. 4,238,565).

The reagent means of the present invention comprises all of the essential chemical elements required to conduct a desired immunoassay method encompassed by the present invention. The reagent means is presented in a commercially packaged form, as a composition or admixture where the compatibility of the reagents will allow, in a test device configuration, or as a test kit, i.e., a packaged combination of one or more containers holding the necessary reagents. Included in the reagent means are the reagents appropriate for the binding reaction system desired, e.g., an antibody and labeled conjugate of the present invention. Of course, the reagent means can include other materials as are known in the art and which may be desirable from a commercial and user standpoint, such as buffers, diluents, standards, and so forth. Particularly preferred is a test kit for the homogeneous competitive binding immunoassay of the present invention comprising (a) an antibody of the present invention and (b) a labeled conjugate which has a detectable property which is altered when bound with the antibody. Also preferred is a test device comprising the reagent composition and a solid carrier member incorporated therewith. The various forms of such test device are described in U.S. patent application Ser. No. 202,378, filed Oct. 30, 1980, now abandoned, which is incorporated herein by reference. The specific label used in the preferred test kit and test device will depend on the technique followed, as described hereinabove.

The present invention will now be illustrated, but is not intended to be limited, by the following examples:

EXAMPLES

Reagents

Italicized numbers appearing after chemical names refer to the structural formulae identified in the text above and/or in the drawings.

A. Preparation of drug derivatives

5-[2-(Cyanoethoxy)-3-dimethylamino]propyl-10,11-dihydro-5H-dibenz[b,f]azepine, (2).

A room temperature solution of 7.0 grams (g) [24 millimoles (mmol)] of 5-(3-dimethylamino-2-hydroxyl)-propyl-10,11-dihydro-5H-dibenz[b,f]azepine (W. Shindler and F. Hafliger, supra) in 50 milliliters (ml) of acrylonitrile was stirred under argon. To it was added, in four portions over a 60 minute period, 1.1 grams (g) of potassium tert-butoxide. The reaction was then quenched with 3.5 ml of glacial acetic acid and concentrated on a rotary evaporator. An orange oil resulted which was adsorbed onto 30 g of neutral alumina. This was placed atop a 38 centimeter (cm) by 4 cm column of alumina made up in ether. The column was eluted with ether. Evaporation of the first liter of eluant gave 6.64 g (80%) yield of 2 as an oil which crystallized on standing (m.p. 56°-61° C.). It was converted to the hydrochloride salt and recrystallized from ethyl acetate (m.p. 157°-159° C.).

Analysis: Calculated for $C_{22}H_{27}N_3$.HCl: C, 68.46; H, 7.31; N, 10.89; Found: C, 68.01; H, 7.08; N, 10.51

5'-[3-Dimethylamino-2-(3-aminopropoxy)]propyl-10,11-dihydro-5H-dibenz[b,f]azepine, (3).

To a cold (0° C.) solution of aluminum hydride ($AlH_3$), prepared from 400 mg (10 mmol) of lithium aluminum hydride and 490 milligrams (mg) [5 mmol] of concentrated sulfuric acid ($H_2SO_4$), in 30 ml of dry tetrahydrofuran (THF) was added, under an inert atmostphere, a solution of 1.8 g (5 mmol) of the nitrile free base 2 dissolved in 10 ml of dry THF. After 2 hours at 0°, an additional 20 mmol of $AlH_3$ in 40 ml of THF was added. The reaction was allowed to warm to room temperature and stir for 12 hours. It was quenched with methanol (MeOH), filtered, and evaporated. The oily residue was chromatographed on 50 g of silica gel eluting with a linear gradient of 2 liters (L) of 9:1 (v/v) chloroform ($CHCl_3$): MeOH to 2 L of 9:1:1 (v/v/v) $CHCl_3$: MeOH: conc. ammonium hydroxide ($NH_4OH$). Ten ml fractions were collected. Fractions 64 through 120 were pooled and evaporated to give 1.7 g (94% yield) of 3 as an oil which was purified by evaporative distillation, b.p. 200°-210° C./0.1 torr.

Analysis: Calculated for $C_{22}H_{31}N_3O$: C, 74,75; H, 8.84; N, 11.89; Found: C, 74.85; H, 8.69; N, 11.28

5-[2-(2-Cyanoethoxy)-3-N-methylamino]propyl-10,11-dihydro-5H-dibenz[b,f]azepine, (7).

To a cold, stirred solution of 4.72 g (17 mmol) of 5-(2-hydroxy-3-N-methylamino)propyl-10,11-dihydro-5H-dibenz[b,f]azepine 5 (W. Shindler and F. Hafliger, supra) in 50 ml of dichloromethane ($CH_2Cl_2$) was added dropwise a solution of 3.65 g (17 mmol) of di-tert-butyl dicarbonate in 20 ml of $CH_2Cl_2$. The reaction was allowed to warm to room temperature and stand for 2 hrs. Solvent was removed under reduced pressure to give the tert-butyloxycarbonyl derivative 6. This was not characterized but was taken up in 20 ml of acrylonitrile and combined with 1 ml of 10% potassium methoxide in MeOH. After 12 hrs. at room temperature, the reaction was acidified with 1.5 ml of glacial acetic acid and evaporated to dryness under reduced pressure. The residue was triturated with 50 ml of warm toluene which was filtered and evaporated to leave 7.14 g of the nitrile 7 as an oil.

Analysis: Mass Spectrum (70 e.v)=m/e 435 [M+].

5-[3-N-Methylamino-2-(3-aminopropoxy)]propyl-10,11-dihydro-5H-dibenz[b,f]azepine, (9).

A mixture of 7.74 g (18 mmol) of 7 in 100 ml of ethanol (EtOH) containing 7.3 g (0.43 mol) of ammonia was hydrogenated over Raney nickel W-2 catalyst (Davidson Speciality Chemical Co., South Pittsburg, TN, USA) at 50° C. and 50 pounds per square inch (psi) hydrogen pressure for 3 hrs. The mixture was cooled, filtered, and evaporated to give 7.32 g of the primary amine 8 as an oil.

Analysis: Mass Spectrum (70 e v): m/e 739 [M+].

A mixture of 1.1 g (2.5 mmol) of 8 and 5 ml of cold trifluoroacetic acid was stirred for 1 hr. at 0° C., then allowed to warm to room temperature for 3 hrs. The excess trifluoroacetic acid was removed under reduced pressure. The oily residue was partitioned between ether and aqueous potassium carbonate ($K_2CO_3$) solution. The layers were separated and the aqueous phase back extracted with $CHCl_3$. The combined organic layers were dried over anhydrous magnesium sulfate ($MgSO_4$), filtered and evaporated. The residue was distilled to give 600 mg (71% yield) of the diamine 9 as an oil, b.p. 200°-210° C. (0.2 torr).

Analysis: Calculated for $C_{21}H_{29}N_3O$: C, 74.30; H, 8.61; N, 12.38; Found: C, 74.56; H, 8.53; N, 12.23

Mass Spectrum (CI): m/e 340 [MH+].

5-(2,3-Epoxypropyl)-5-hydroxy-10,11-dihydro-5H-dibenzo[a,d]cycloheptene (11).

To a stirred, refluxing solution of 35.7 g (0.14 mol) of 5-allyl-5-hydroxy-10,11-dihydro-5H-dibenzo[a,d]cycloheptene 10 (R. D. Hoffsommer, et al, supra) in 500 ml of hexane was added 0.5 g of vanadium (III) acetylacetonate followed by the dropwise addition of 25.1 g (0.22 mol) of 70% tert-butylhydroperoxide. The resulting yellow mixture was refluxed for 4 hrs., then 100 ml of toluene was added. The reaction was allowed to cool to room temperature and stand for 12 hrs. Excess hydroperoxide was destroyed by the addition of 300 ml of aqueous sodium sulfite ($Na_2SO_3$) solution (10%). The organic phase was separated, dried over anhydrous $MgSO_4$, filtered and evaporated. Recrystallization of the solid from $CHCl_3$-hexane gave 18.5 g (50% yield) of the epoxide 11, m.p. 116°-118° C.

Analysis: Calculated for $C_{18}H_{18}O_2$: C, 81.17; H, 6.81; Found: C, 81.03; H, 6.82

5-(3-Dimethylamino-2-hydroxypropyl)-5-hydroxy-10,11-dihydro-5H-dibenzo[a,d]cycloheptene (12).

A mixture of 3.7 g (14 mmol) of the epoxide 11, 26.8 g (0.59 mol) of anhydrous dimethylamine, and 50 ml of EtOH was heated at 100° C. in a stainless steel autoclave for 12 hrs. When cool the contents were removed and concentrated under reduced pressure. Recrystallization of the solid residue from aqueous EtOH afforded 1.6 g (37% yield) of the crystalline amino-diol 12, m.p. 144°–146° C.

Analysis: Calculated for $C_{20}H_{25}NO_2$: C, 77,13; H, 8.09; N, 4.50; Found: C, 76.94; H, 8.34; N, 4.73

5-(3-Dimethylamino-2-hydroxypropylidinyl-1)-10,11-dihydro-5H-dibenzo[a,d]cyclo-heptene, (13).

The amino-diol 12 (10.4 g, 33 mmol) was dissolved in 200 ml of 3N hydrochloric acid (HCl) and allowed to stand for 30 min. It was then made basic with $K_2CO_3$, extracted with ether, and the ether phase separated, dried, and evaporated. The residue was converted to the HCl salt and recrystallized from acetone-ethyl acetate to give 6.5 g (60% yield) of the HCl salt of 13, m.p. 202°–204° C. (cf J. R. Boissier, et al, German OLS 1,913,701; Oct. 9, 1969, Chem. Abst. 72, P4329Sd).

5-[2-(2-Cyanoethoxy)-3-dimethylaminopropylidinyl-1]-10,11-dihydro-5H-dibenzo[a,d]cycloheptene, (14).

To a stirred solution of 6.9 g (23 mmol) of the free base 13 in a mixture of 100 ml of acrylonitrile and 100 ml of THF was added 500 mg of potassium tert-butoxide. After 12 hrs. at room temperature, the reaction was acidified with 5 ml of glacial acetic acid, filtered, and evaporated under reduced pressure. The residue was chromatographed on 100 g of silica gel eluting with a linear gradient of 2 L of $CHCl_3$ to 2 L of 4:1 (v/v) $CHCl_3$:EtOH; 20 ml fractions were collected. Fractions 161–200 were pooled and evaporated to give an oil. It was taken up in ether, filtered, washed with aqueous sodium bicarbonate solution, filtered, and evaporated to give 3 g (38% yield) of the nitrile 14 as a clear oil.

Analysis: Mass Spectrum (CI): m/e 347 [MH+]; 276 [M+ minus $OCH_2CH_2CN$].

5-[2-(3-Aminopropoxy)-3-dimethylaminopropylidinyl-1]-10,11-dihydro-5H-dibenzo[a,d]cycloheptene, (15).

An ice-cold solution of the nitrile 14 (3.02 g, 8.7 mmol) in 50 ml of EtOH was saturated with gaseous ammonia, combined with W-2 grade Raney nickel catalyst, and shaken under 50 psi of hydrogen pressure at 55° C. for 5 hrs. The mixture was then cooled, filtered, and the solvent evaporated to give a residue which was chromatographed on 100 g of silica gel eluting with 19:1 (v/v) EtOH: concentrated $NH_4OH$. Twenty ml fractions were collected. Fractions 16–121 were pooled and evaporated to give a 2.71 g (89% yield) of the primary amine 15 as an oil.

Analysis: Mass Spectrum (CI): m/e 351 [MH+], 276 [M+ minus $OCH_2CH_2CH_2NH_2$].

5-(2-Hydroxy-3-N-methylaminopropyl)-5-hydroxy-10,11-dihydro-5H-dibenzo[a,d]cycloheptene, (16).

A mixture of 10 g (38 mmol) of the epoxide 11, 30 g (0.96 mol) of methylamine, and 100 ml of EtOH was heated in a stainless steel autoclave for 12 hrs. at 80° C. When cool, the contents were removed, filtered, and solvent evaporated under reduced pressure. The solid residue was recrystallized from aqueous EtOH to give 10.3 g (90% yield) of the amino-diol 16 as a white solid, m.p. 140°–143° C.

Analysis: Calculated for $C_{19}H_{23}NO_2$: C, 76.73; H, 7.80; N, 4.71; Found: C, 77.08; H, 7.61; N, 4.27

5-(2-Hydroxy-3-N-methylpropylidinyl-1)-10,11-dihydro-5H-dibenzo[a,d]cycloheptene, (17)

A solution of amino-diol 16 (15 g, 50 mmol) in 150 ml of 3N HCl was allowed to stand for 2 hrs., then made basic with ammonium hydroxide and extracted into $CHCl_3$. Evaporation gave an oil which was crystallized from ether to give 10.5 g (75% yield) of 17 as a solid, m.p. 112°–114° C.

Analysis: Calculated for $C_{19}H_{21}NO$: C, 81.68; H, 7.58; N, 5.01; Found: C, 81.61; H, 7.36; N, 5.00

5-[2-(2-Cyanoethoxy)-3-(N-tert-butyloxycarbonyl-N-methylamino)propylidinyl-1]-10,11-dihydro-5H-dibenzo[a,d]cycloheptene, 19

To a stirred solution at room temperature of 10.5 g (38 mmol) of the amine 17 in 190 ml of $CH_2Cl_2$ was added 8.29 g (38 mmol) of di-tert-butyl dicarbonate. One hr. later, solvent was removed under reduced pressure to give the intermediate 18 as a oil. It was not characterized but was dissolved in 150 ml of acrylonitrile. To this was added, at hourly intervals, 4–100 mg portions of potassium tert-butoxide after which stirring was continued for an additional 12 hrs. The reaction was acidified with 3 ml of glacial acetic acid, filtered, and evaporated. This left a residue which was purified by preparative high pressure liquid chromatography (HPLC) eluting with 19:1 (v/v) $CHCl_3$: ethyl acetate to give 10.6 g (64% yield) of the nitrile 19 as an oil.

Analysis: Mass Spectrum (70 ev): m/e 432 [M+ minus isobutylene].

5-[2-(3-Aminopropoxy)-3-(N-tert-butyloxycarbonyl-N-methylamino)propylidinyl-1]-10,11-dihydro-5H-dibenzo[a,d]cycloheptene, (20)

A mixture of 2.56 g (6 mmol) of the nitrile 19, W-2 grade Raney nickel catalyst, and 50 ml of EtOH saturated with ammonia gas was shaken under an atmosphere of hydrogen (50 psi) for 5 hrs. at 60° C. It was then filtered, and the filtrate evaporated under reduced pressure to leave an oil. The oil was chromatographed on 60 g of silica gel eluting with 2.5% concentrated ammonium hydroxide in EtOH and collecting 15 ml fractions. Fractions 91–121 were pooled and evaporated to give 2 g (77% yield) of amine 20 as an oil.

Analysis: Mass Spectrum (70 ev): m/e 436 [M+].

5-[2-(3-Aminopropoxy)-3-(N-methylamino)propylidinyl-1]-10,11-dihydro-5H-dibenzo[a,d]cycloheptene, (21)

The tert-butyloxycarbonyl derivative 20 (2.5 g, 6 mmol) was dissolved in 100 ml of (1:1) 3N HCl and 2-propanol and allowed to stand at room temperature for 1 hr., then made basic with $K_2CO_3$ and extracted into $CHCl_3$. The extract was dried, filtered, and evaporated to give an oily residue which was chromatographed on 100 g of silica gel, eluting with 3 L of 1% concentrated ammonium hydroxide in EtOH. Fifteen ml fractions were collected and the product eluted in fractions 282–401. These were pooled and evaporated to give 340 mg (17% yield) of the di-amine 21 as an oil.

Analysis: Mass Spectrum (CI): m/e 337 [MH+].

B. Preparation of immunogens

Amitriptyline immunogen 2.5 ml of 50% (v/v) aqueous THF was added to a vial containing 250 mg (714 μmol) of the amino-derivative of amitriptyline 15. The pH of the resulting solution was adjusted to 4.5 with 5M HCl. 118 mg (1.76 μmol) of Pentex bovine serum albumin (Research Products Division, Miles Laboratories, Inc., Elkhart, Ind.) was added to the solution and the pH readjusted to 4.5 after complete dissolution of the protein. The solution was cooled in an ice bath and 380 mg (1.98 μmol) of EDC (1-ethyl-3(3-dimethylaminopropyl)carbodiimide hydrochloride) was added with stirring. After one hour at 0° C., the reaction was transferred to a 4° C. cold room, where it was kept for 23 more hours with stirring.

The labeled serum albumin was isolated by chromatography at room temperature on a Sephadex G-25 fine (Pharmacia Fine Chemicals, Piscataway, N.J.) column (1.5×55 cm). The column was pre-equilibrated and eluted with 50 mM sodium acetate, pH 5.0. 1.4 ml fractions were collected and the absorbances at 280 nm were determined. Those fractions containing the immunogen (tubes 19–29) were pooled to give a total volume of 15.6 ml. After determining the protein concentration [Lowry et al, *J. Biol. Chem.* 193: 265(1951)], the substitution level (epitopic density) of drug in serum albumin was determined to be 9.1 by using the absorbance of the pooled fractions at 280 nm. For these calculations molar extinction coefficients at 280 nm of $4.4 \times 10^4 M^{-1} cm^{-1}$ and $674 M^{-1} cm^{-1}$ were used for bovine serum albumin and amitriptyline, respectively.

Desipramine immunogen

Distilled water (5 ml) was used to dissolve 240 mg (707 μmol) of the amino-derivative of desipramine 9, to give a cloudy solution. After adjusting the pH of the solution to 4.5 with HCl, 75 mg (1.12 μmol) of Pentex bovine serum albumin was added. The pH of the solution was readjusted to 4.5 with HCl, and the solution cooled to 5° C. on an ice bath. To this solution was added 125 mg (625 μmol) of EDC with stirring. The reaction was kept on an ice bath for one hour, then transferred to a 4° C. cold room where it was allowed to stand with stirring overnight.

The immunogen was isolated by purification on a Sephadex G-25 fine column (1.5×45 cm) by room temperature elution with 50 mM sodium acetate buffer, pH 5. Fractions (4.5 ml) were collected and their absorbances at 280 nanometers (nm) determined. Those fractions containing bovine serum albumin (12–16) were pooled. The epitopic density on the bovine serum albumin was determined to be 25.2 by the methods described for the amitriptyline immunogen, using a molar extinction coefficient at 280 nm of $5.87 \times 10^3 M^{-1} cm^{-1}$ for the desipramine derivative.

Imipramine immunogen

This was prepared essentially as described for the desipramine immunogen. 150 mg (424 μmol) of the amino-derivative of imipramine 3 was dissolved in 5 ml of water to give a cloudy solution whose pH was adjusted to 4.5 with HCl. After the addition of 50 mg (0.746 μmol) of Pentex bovine serum albumin, the pH was again adjusted to 4.5 and the aqueous mixture cooled to 5° C. in an ice bath. 125 mg (652 μmol) of EDC was added with stirring and the reaction kept on ice for an hour, after which it was transferred to a cold room (4° C.) and was stirred overnight.

The immunogen was isolated by gel exclusion chromatography as described for desipramine; 2.5 ml fractions were collected and their absorbances at 280 nm determined. Fractions 9–13 contained the substituted bovine serum albumin and were pooled. Using the methods described for the other immunogens, the substitution level of the immunogen was determined to be 44.7, assuming a molar extinction coefficient at 280 nm of $4.31 \times 10^3 M^{-1} cm^{-1}$ for the imipramine derivative.

C. Preparation of labeled conjugates

5-[[3-Dimethylamino-2-[3-(7-β-galactosylcoumarin-3-carboxamido)propoxy]propyl]]-10,11-dihydro-5H-dibenz[b,f]azepine, (26a)

A solution of 1.55 g (4 mmol) of 7-β-galactosylcoumarin-3-carboxylic acid (U.S. Pat. No. 4,226,978) in 40 ml of dry DMF containing 2 g of 3 angstrom molecular sieves was stirred for 3 hours under an inert atmosphere, then cooled to −10° C. and combined with 400 mg (4 mmol) of triethylamine. Isobutyl chloroformate (550 mg, 4 mmol) was added and stirring continued at −10° for 20 min. To this was added 1.41 g (4 mmol) of the primary amino compound 3 in 20 ml of DMF. After 12 hrs. the reaction mixture was filtered, 20 g of silica gel added, and the solvent evaporated. The impregnated silica gel was placed atop a column of 100 g of silica gel made up in ethanol. It was eluted with a linear gradient of 2 L of ethanol to 2 L of 9:1 (v/v) ethanol: 1M aqueous triethylammonium bicarbonate. Ten ml fractions were collected. Fractions 40 through 140 were pooled and evaporated to give 2 g (71% yield) of the labeled imipramine conjugate 26a as a yellow viscous oil, which was converted to the hydrochloride salt, m.p. 148° C. (dec).

Analysis: Calculated for $C_{38}H_{45}N_3O_{10} \cdot HCl \cdot H_2O$: C, 61.65; H, 6.26; N, 5.68; Found: C, 61.02; H, 6.38; N, 5.67

Optical Rotation: $\alpha_D = 144.47°$ (c 1.0, MeOH)

4-[2-(7-β-Galactosylcoumarin-3-carboxamido)ethyl]-piperazine-1-acetic acid, (26b)

1-(2-Aminoethyl)piperazine was converted to the N-trifluoroacetamide derivative by treatment with ethyl trifluoroacetate. Recrystallization from toluene gave white needles, m.p. 92°–93° C.

Analysis: Calculated for $C_8H_{14}F_3N_3O$: C, 42.66; H, 6.25; N, 18.66; Found: C, 42.68; H, 5.85; N, 19.12

1-(2-Trifluoroacetamidoethyl)piperazine (56 g, 0.25 mol), 37.5 ml of triethylamine, and 30.3 g (0.27 mol) of ethyl chloroacetate were combined in 200 ml of DMF. The temperature rose to 70° C. in 5 minutes. The reaction was allowed to stir overnight at room temperature, then filtered to remove triethylammonium hydrochloride. The solvent was removed, leaving an oily residue which was taken up in 250 ml of CHCl$_3$ and washed with two 300 ml portions of H$_2$O. The organic phase was separated, dried and evaporated to give 51 g of ethyl 4-(2-trifluoroacetamidoethyl)piperazine-1-acetate as a tan solid. This was not characterized. It was hydrolyzed by stirring for 6 hours in a solution of 20 g of KOH in 250 ml of 4:1 MeOH:H$_2$O. The product was purified by chromatography on 1400 g of silica gel, eluting with 4:4:1 (v/v/v) CHCl$_3$:MeOH:conc. NH$_4$OH. Recrystallization from MeOH gave 22.5 g of 4-(2-aminoethyl)piperazine-1-acetic acid as white crystals, m.p. 225° C. (dec).

A mixture of 2.6 g (6.5 mmol) of 7-β-galactosylcoumarin-3-carboxylic acid, supra, 730 mg (6.5 mmol) of N-hydroxysuccinimide and 1.3 g (6.3 mmol) of dicyclohexylcarbodiimide in 40 ml of DMF was stirred at room temperature for 36 hours. It was filtered to remove the precipitated dicyclohexyl urea, and the filtrate added dropwise to a cold solution of 1.2 g (6.4 mmol) of 4-(2-aminoethyl)piperazine-1-acetic acid in 40 ml of H$_2$O. To this was added 520 mg (6.2 mmol) of NaHCO$_3$ and the reaction allowed to warm to room temperature overnight. The precipitate which formed was recrystallized from H$_2$O:2-propanol giving 2.2 g of 4-[2-(7-β-galactosylcoumarin-3-carboxamido)ethyl]piperazine-1-acetic acid (the label acid derivative) as a white solid. A 250 mg sample was recrystallized from H$_2$O:methanol yielding 180 mg of white crystals, m.p. 187°–192° C.

Analysis: Calculated for C$_{24}$H$_{31}$O$_{11}$.H$_2$O: C, 51.89; H, 5.98; N, 7.46; Found: C, 51.87; H, 5.90; N, 7.90

To a slurry of the label acid derivative (540 mg, 1 mmol) in 25 ml of dry DMF was added 180 mg (1.4 mmol) of diisopropyl ethylamine and the mixture warmed briefly to 60° C., then cooled to 0° C. Isobutyl chloroformate (140 mg, 1 mmol) was added and the reaction stirred at 0° C. for 1 hour. The amine 3 (360 mg, 1 mmol), dissolved in 10 ml of DMF was added, and the reaction allowed to warm to room temperature and stir for 12 hours. The solvent was removed on a rotary evaporator attached to a vacuum pump. The residue was chromatographed on 100 g of silica gel eluting with 2 L of ethyl acetate, 4 L of ethanol, then 2 L of 9:1 (v/v) ethanol:1M aqueous triethylammonium bicarbonate. Fifteen ml fractions were collected. Fractions 642 through 681 were pooled, filtered, and evaporated. The residue was recrystallized from hot ethanol to give 150 mg (15% yield) of the labeled conjugate 26b, m.p. 140°–143° C.

Analysis: Calculated for the bis-carbonate salt C$_{48}$H$_{64}$N$_6$O$_{17}$: C, 57.82; H, 6.47; N, 8.47; Found: C, 56.99; H, 6.64; N, 8.04

FAD-imipramine conjugate, 27a

A solution of 2.87 g (10 mmol) of 6-chloro-9β-D-ribofuranosyl-9H-purine [K. Mosbach, "Methods in Enzymology", vol. 34, part B(1974) page 230] in 50 ml of dry THF was combined with 9.01 g (20 mmol) of 2,2,2-tribromoethylphosphoromorpholinochloridate [J. H. van Boom, R. Crea, W. C. Lyuten, A. B. Vink, *Tet. Lett.* 2779 (1975)] and stirred at room temperature for 48 hours. It was evaporated to dryness and the oily residue partitioned between 300 ml of CHCl$_3$ and 200 ml of 1N HCl. The organic phase was separated, washed with an additional 200 ml of 1N HCl, dried over anhydrous MgSO$_4$, and evaporated to give a red oil. This was purified by preparative liquid chromatography on silica gel eluting with 9:1 (v/v) CHCl$_3$:EtOH to give 2 g (28% yield) of the 5'-(2,2,2-tribromoethylmorpholino)phosphate ester of 6-chloro-9β-D-ribofuranosyl-9H-purine as a glassy white solid.

Analysis: Calculated for C$_{16}$H$_{20}$Br$_3$ClPN$_5$O$_7$: C, 27.43; H, 2.88; N, 10.00; Found: C, 27.77; H, 2.79; N, 8.63

The 6-chloropurine (0.8 g, 2.6 mmol) was dissolved in 10 ml of dry DMF together with 450 mg (2.75 mmol) of ethyl 5-aminocaproate and 525 mg of triethylamine. After 18 hr. at room temperature the solvent was removed under reduced pressure, and the residue purified on a preparative liquid chromatograph eluting with 9:1 (v/v) CHCl$_3$:EtOH. This gave 1.5 g (64% yield) of the 5'-(2,2,2-tribromoethylmorpholino)phosphate ester of N$^6$-(5-carbethoxypentyl)adenosine as a tan glass.

Analysis: Calculated for C$_{24}$H$_{36}$Br$_3$PN$_6$O$_9$: C, 35.01; H, 4.41; N, 10.21; Found: C, 35.08; H, 4.70; N, 10.31

A solution of 3.4 g (4.2 mmol) of this nucleotide derivative in 50 ml of dry pyridine was combined with 1 ml of 2,4-pentanedione and 5 g of zinc-copper couple [Adamiak et al, *Nucleic Acids Research* 4:2321 (1977)]. After stirring for several minutes, the temperature rose to 30° C. and the flask was immersed in an ice bath until the temperature cooled to 20° C. After 15 more minutes at this temperature the zinc was removed by filtration. The light yellow filtrate was concentrated under reduced pressure and the oily residue taken up in 2 L of 50% aqueous EtOH. This was applied to a 60 cm × 5 cm column of Sephadex A-25 (Pharmacia Fine Chemicals, Piscataway, N.J., USA) which had been equilibrated with 1M aqueous triethylammonium bicarbonate, then washed with 2 L of 50% aqueous EtOH. After the sample was applied, the column was washed with a linear gradient of 2 L of 50% aqueous EtOH to 2 L of H$_2$O. The washings were discarded. The column was then eluted with a linear gradient of 4 L of H$_2$O to 4 L of 0.5M triethylammonium bicarbonate. Nineteen ml fractions were collected. Fractions 171–206 were pooled and evaporated to give 1.54 g (56% yield) of the triethylammonium salt of the morpholide of N$^6$-(5-carbethoxypentyl)adenosine monophosphate as a yellow glassy solid.

This solution was lyophilized overnight. The resulting solid was taken up in dry DMF and reconcentrated under reduced pressure. It was then reacted with 2 equivalents of 5'-flavin mononucleotide by the procedure of Moffatt & Khorana, *J. Amer. Chem. Soc.* 83: 649 (1961). The completed reaction was diluted with 2 L of H$_2$O and applied to a 38 cm × 4 cm column of DEAE-cellulose (DE-53, Whatman, Inc., Clifton, N.J., USA) acetate form. The column was eluted with a linear gradient of 4 L H$_2$O to 4 L of 0.6M aqueous ammonium acetate, pH 4.6. Twenty five ml fractions were collected. Fractions 370 through 430 were pooled and reduced to 300 ml on the rotary evaporator. This was concentrated to 50 ml on an Amicon membrane filter (Amicon Corp., Lexington, MA, USA) with a 500 molecular weight cut off. It was diluted to 300 ml and the process repeated. The residual ammonium acetate was removed by passing the solution through a 126 cm × 5 cm column of Bio Gel P-2, 200–400 mesh (Bio-Rad Laboratories, Richmond, Calif., USA) with H$_2$O as eluant at a flow rate of 0.34 ml/min. Ten ml fractions were collected. Fractions 57–127 were pooled and concentrated to 33 ml volume. The yield of N$^6$-(5-carbethoxypentyl)FAD was determined to be 365 micromoles (16%) based on the millimolar extinction coefficient at 450 nm of FAD (11.3).

The pH of this solution was adjusted to 12 with 1N NaOH. After 5 hrs., the pH was lowered to 7.4 and the volume reduced to 24 ml under reduced pressure. The solution was applied to the Bio Gel P-2 column used previously, eluting with H$_2$O at a flow rate of 0.6 ml/min. Eighteen ml fractions were collected. Fractions 35 to 92 were pooled and the yield of N$^6$-(5-carboxypentyl)FAD determined by spectroscopy to be 300 micromoles.

A mixture of 28 mg (80 micromoles) of 5-(3-dimethylamino-2-(3-aminopropoxy)]propyl-10,11-dihydro-5H-dibenz[b,f]azepine 3 and 1.4 ml of a 14.2 millimolar solution of N$^6$-(5-carboxypentyl)FAD was cooled to 4° C., adjusted to pH 5.6 with 0.1N HCl, and combined with 15 mg of 1-(3-dimethylaminopropyl)-3-ethylcarbodiimide hydrochloride. After 18 hrs. at this temperature, 1 g of silicic acid was added and the solvent removed under reduced pressure. The impregnated adsorbent was placed atop a 45 cm × 2 cm column of silicic acid made up in 19:1 (v/v) EtOH:1M aqueous triethylammonium bicarbonate. The column was eluted with 500 ml of this solvent followed by 2 L of 1:1 (v/v) EtOH:1M triethylammonium bicarbonate. Ten ml fractions were collected. Fractions 77–103 were pooled and evaporated to dryness. The residue was taken up in a small volume of aqueous ethanol and passed over a small column of Amberlite IRC-50 ion exchange resin (triethylammonium form) (Mallinckrodt, Inc., St. Louis, MO, USA). Complete purification was achieved by HPLC using a Whatman ODS-3 Magnum 9 C-18 reverse phase column (Alltech Associates, Inc., Deerfield, IL, USA) eluting with 9:1 (v/v) acetonitrile:$H_2O$. The FAD-labeled imipramine conjugate 27a was obtained in 2% yield (0.4 micromoles).

5-[[3-N-Methylamino-2-[3-(7-$\beta$-galactosylcoumarin-3-carboxamido)propoxy]propyl]]-10,11-dihydro-5H-dibenz[b,f]azepine, (26b)

The amine 8 (1.76 g, 4 mmol) was reacted with 1.55 g (4 mmol) of 7-$\beta$-galactosylcoumarin-3-carboxylic acid by the procedure used to prepare conjugate 26a. The crude product was chromatographed on silica gel eluting with EtOH. Fractions containing the product were pooled and evaporated to give 2.08 g of an oil. This was dissolved in 10 ml of cold trifluroacetic acid, and after 30 minutes, evaporated at 0° C. under high vacuum. The residue was taken up in $H_2O$ and made basic with sodium bicarbonate ($NaHCO_3$). A precipitate formed which was filtered and chromatographed on 120 g of silica gel, eluting with EtOH. The product eluted (20 ml fractions) from fractions 161–730. These were pooled, evaporated, and the residue recrystallized from EtOH to give 940 mg (34% yield) of the labeled desipramine conjugate 26c.

Analysis: Calculated for $C_{37}H_{45}N_3O_{11}$: C, 62.79; H, 6.41; N, 5.94; Found: C, 62.54; H, 6.47; N, 5.66

5-[[3-Dimethylamino-2-[2-(7-$\beta$-galactosylcoumarin-3-carboxamido)propoxy]propylidinyl-1]]-10,11-dihydro-5H-dibenzo[a,d]cycloheptene, (26d)

The amine 15 (790 mg, 2.2 mmol) was reacted with the label acid 7-$\beta$-galactosylcoumarin-3-carboxylic acid in the same manner as for labeled conjugates 26a and 26c. The product was purified by chromatography on 60 g of silica gel, eluting with 1 L of ethyl acetate, then with EtOH. Five ml fractions were collected. Fractions 52–201 were pooled and evaporated to give 320 mg (18% yield) of the labeled amitriptyline conjugate 26d as a solid, m.p. 140°–145° C.

Immunoassay Methods

A. Amitriptyline antiserum titration

1. Reagents
   a. Enzyme Reagent-50 mM Bicine buffer [N,N-bis-(2-hydroxyethyl)glycine, Calbiochem-Behring Corp., LaJolla, Calif. USA], pH 8.5 containing 1.5 unit/ml $\beta$-galactosidase and 15.4 mM sodium azide.
   b. Fluorogenic Reagent-5 mM formate buffer, pH 3.5, containing 0.538 $\mu$M of the $\beta$-galactosyl-umbelliferoneamitriptyline conjugate 26d, 0.01% (v/v) Triton X-100 [Calbiochem-Behring Corp., LaJolla, Calif. USA] and 3.08 mM sodium azide.
   c. Amitriptyline standards-USP amitriptyline hydrochloride was added to normal human serum containing 3.08 mM sodium azide.
   d. Buffer-50 mM Bicine pH 8.5 with 15.4 mM sodium azide.
2. Titration method
   Using an Ames Diluter (Ames Division, Miles Laboratories, Inc., Elkhart, Ind. USA) the following were added to polystyrene cuvettes (Evergreen Scientific, Los Angeles, Calif. USA) in the order given:
   a. 100 $\mu$l of Enzyme Reagent+900 $\mu$l Buffer
   b. 1 ml Buffer+antiserum to be titrated (raised against amitriptylline immunogen, supra)
   c. 100 $\mu$l Fluorogenic Reagent+900 $\mu$l Buffer
   Addition of the Fluorogenic Reagent was followed by mixing the cuvettes' contents. The fluorescence intensity was determined for each cuvette 20 minutes after addition of the Fluorogenic Reagent (excitation 400 nm, emission 450 nm).
   Three sets of cuvettes were prepared in parallel as follows:
   High Standard:
     contained 25 $\mu$l of amitriptyline high standard (400 ng/L). This was added prior to the addition of Fluorogenic Reagent.
   Low Standard:
     contained 25 $\mu$l of amitriptyline zero standard. This was added prior to the addition of Fluorogenic Reagent.
   Blank:
     This set of cuvettes was identical to the low standard set except that 100 $\mu$l of buffer was used in place of Fluorogenic Reagent.
3. Results
   The two point titration of the antibody gave the following results after subtraction of blank fluorescence and normalization:

|                          | Normalized Fluorescence | |
| ------------------------ | --------------- | ------------ |
| Volume of Antiserum ($\mu$l) | High Standard   | Low Standard |
| 0                        | 100             | 100          |
| 1                        | 95.7            | 94.4         |
| 2                        | 91.9            | 86.0         |
| 3                        | 89.3            | 79.2         |
| 4                        | 85.7            | 66.8         |
| 6                        | 78.4            | 58.1         |
| 8                        | 70.2            | 46.7         |
| 10                       | 60.8            | 38.8         |

B. Desipramine antiserum titration

1. Reagents
   a. The enzyme, buffer and fluorogenic reagents used were identical to those employed in the titration of amitriptyline antiserum.
   b. High standard-400 ng/L USP nortriptyline in 50 mM Bicine, pH 8.3, 15.4 mM sodium azide and 0.01% (v/v) Triton X-100.
2. Titration method
   The method described previously for the titration of amitriptyline antiserum was used.
3. Results
   After subtraction of the appropriate blank fluorescence and normalization, the following results were obtained:

|                          | Normalized Fluorescence | |
| ------------------------ | --------------- | ------------ |
| Volume of Antiserum ($\mu$l) | High Standard   | Low Standard |
| 0                        | 100             | 100          |
| 5                        | 97.1            | 88.9         |
| 10                       | 92.2            | 77.7         |
| 20                       | 83.3            | 60.7         |

C. Immunoassay for nortriptyline

A substrate-labeled fluorescent immunoassay (SLFIA, see U.S. Pat. No. 4,279,992) was demonstrated for nortriptyline as follows:

1. Reagents
   a. Antibody/Enzyme Reagent-50 mM Bicine buffer, pH 8.3, containing 0.15 units/ml of β-galactosidase, sufficient imipramine antiserum to decrease fluorescence observed after 20 min. to 15% of that in the absence of antiserum, and 15.4 mM sodium azide.
   b. Fluorogenic Reagent-30 mM formate buffer, pH 3.5, 0.538 μM of the β-galactosyl-umbelliferone-amitriptyline conjugate 26d and 0.01% (v/v) Triton X-100.
   c. Nortriptyline standards-USP nortriptyline hydrochloride added to normal human serum containing 3.08 mM sodium azide. Immediately before the assay the serum standards were diluted four-fold with 50 mM Bicine buffer, pH 8.3, containing 15.4 μM sodium azide.
   d. Buffer-50 mM Bicine buffer, pH 8.3, containing 15.4 μM sodium azide.

2. Assay protocol

The immunoassay was performed using an Ames Diluter and polystyrene disposable cuvettes (Evergreen Scientific Corp., Los Angeles, Calif.). Reagent solutions were added to the cuvettes in the order given below:
   1. 50 μl Antibody/Enzyme Reagent + 500 μl buffer
   2. 50 μl diluted serum standard + 500 μl buffer
   3. 50 μl Fluorogenic Reagent + 500 μl buffer The Fluorogenic Reagent was added to each cuvette at timed intervals, after which the contents of the cuvette were thoroughly mixed. A "blank" cuvette was also prepared in which buffer was substituted for Fluorogenic Reagent. Twenty minutes after addition of the Fluorogenic Reagent the fluorescence intensity of each solution was determined (excitation 400 nm, emission 450 nm).

3. Results

The immunoassay for nortriptyline gave the following results after subtraction of blank fluorescence and normalization:

| Nortriptyline (ng/ml) | Normalized Fluorescence |
|---|---|
| 0 | 43.4 |
| 50 | 49.2 |
| 100 | 59.7 |
| 200 | 73.5 |
| 300 | 81.6 |
| 400 | 90.0 |

Nortriptyline concentrations in unknown samples could thus be determined by applying the SLFIA protocol to such samples and comparing resulting fluorescence to the above-established standard curve.

D. Immunoassay for imipramine

An apoenzyme reactivation immunoassay system (ARIS, see U.S. Pat. No. 4,238,565) was established for imipramine as follows:

1. Reagents
   a. Apoenzyme Reagents-1.5 μM apoglucose oxidase (U.S. Pat. No. 4,268,631), 100 μl/ml antiserum to glucose oxidase, 3.5 μl/ml antiserum to imipramine, 4 mM 4-aminoantipyrine, 15% (w/v) glycerol, and 0.1M phosphate buffer, pH 7.0.
   b. Label Reagent-4.0 nM of the FAD-imipramine conjugate 27a, 2.1 mM sodium 3,5-dichloro-2-hydroxybenzene sulfonate, 21 μg/ml peroxidase, 1.05M glucose, and 0.1M phosphate buffer, pH 7.0, 2. Assay protocol Serum samples to be assayed were diluted 10-fold with 0.1M phosphate buffer, pH 7.0, containing 0.1% (w/v) BSA. The diluted samples (50 μl) and 1.9 ml of Label Reagent were mixed in disposable cuvettes and equilibrated to 37° C. Apoenzyme Reagent (100 μl) was then dispensed into cuvette caps. The reaction was started by placing the caps on the cuvettes and inverting several times for mixing. The cuvettes were then incubated at 37° C. for 5 minutes and the absorbance at 520 nm recorded.

3. The results were as follows (the average of duplicates):

| Imipramine (ng/ml) | Absorbance |
|---|---|
| 0 | 0.505 |
| 50 | 0.559 |
| 100 | 0.624 |
| 200 | 0.744 |
| 300 | 0.879 |
| 400 | 0.998 |

Imipramine concentrations in unknown samples could thus be determined by applying the ARIS protocol to such samples and comparing resulting absorbance at 520 nm to the above-established curve.

What is claimed is:

1. A tricyclic antidepressant drug immunogen of the formula:

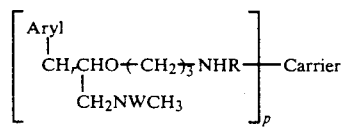

wherein Aryl represents a tricyclic antidepressant drug nucleus selected from the group consisting of

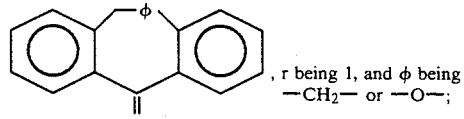

A., r being 1, and φ being —CH$_2$— or —O—;

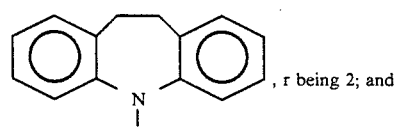

B., r being 2; and

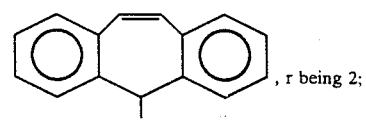

C., r being 2;

wherein W is hydrogen or methyl; R is a bond or a linking group; Carrier is an immunogenic carrier material; and p is on the average from 1 to about 50.

2. The immunogen of claim 1 wherein said linking group is a chain comprising between 1 and 20 atoms, excluding hydrogen.

3. The immunogen of claim 2 wherein said chain is aliphatic.

4. The immunogen of claim 1 wherein said carrier material is a protein or polypeptide.

5. The immunogen of claim 4 wherein R is a bond forming an amide couple to carboxyl groups in said carrier.

6. The immunogen of claim 5 wherein said carrier material is an albumin.

7. An imipramine or desipramine immunogen of the formula:

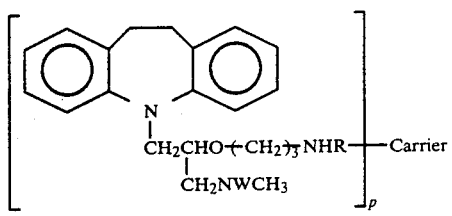

wherein W is hydrogen or methyl, R is a bond or a linking group, Carrier is an immunogenic carrier material, and p is on the average from 1 to about 50.

8. The immunogen of claim 7 wherein said linking group is a chain comprising between 1 and 20 atoms, excluding hydrogen.

9. The immunogen of claim 7 wherein said carrier material is a protein or polypeptide and R is a bond forming an amide couple to carboxyl groups in said carrier.

10. The immunogen of claim 9 wherein said carrier material is an albumin.

11. An amitriptyline or nortriptyline immunogen of the formula:

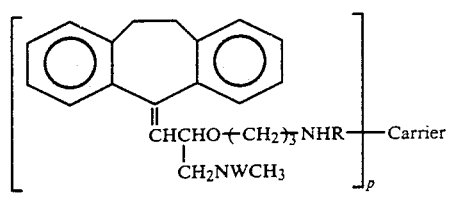

wherein W is hydrogen or methyl, R is a bond or a linking group, Carrier is an immunogenic carrier material, and p is on the average from 1 to about 50.

12. The immunogen of claim 11 wherein said linking group is a chain comprising between 1 and 20 atoms, excluding hydrogen.

13. The immunogen of claim 11 wherein said carrier material is a protein or polypeptide and R is a bond forming an amide couple to carboxyl groups in said carrier.

14. The immunogen of claim 13 wherein said carrier material is an albumin.

15. An antibody prepared against the immunogen of claim 1.

16. An antibody prepared against the immunogen of claim 7.

17. An antibody prepared against the immunogen of claim 11.

18. In an immunoassay method for determining a tricyclic antipressant drug,
the improvement which comprises employing an antibody of claim 15 as the antibody to the tricyclic antidepressant drug.

19. In reagent means for determining a tricyclic antidepressant drug by immunoassay,
the improvement which comprises employing an antibody of claim 15 as the antibody to the tricyclic antidepressant drug.

20. A test kit for determining a tricyclic antidepressant drug by homogeneous immunoassay, comprising (a) an antibody of claim 15 and (b) a labeled conjugate of the drug under assay which has a detectable property which is altered when bound with said antibody.

21. A test device for determining a tricyclic antidepressant drug by homogeneous immunoassay, comprising (a) a reagent composition including an antibody of claim 15 and a labeled conjugate of the drug under assay which has a detectable property which is altered when bound with said antibody, and (b) a solid carrier member incorporated with said reagent composition.

* * * * *